US00PP20353P2

(12) United States Plant Patent
Hanes

(10) Patent No.: US PP20,353 P2
(45) Date of Patent: Sep. 22, 2009

(54) *VERBENA* PLANT NAMED 'LAN PURSAR'

(50) Latin Name: *Verbena hybrida*
Varietal Denomination: Lan Pursar

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/150,461

(22) Filed: Apr. 28, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Susan B McCormick Ewoldt
(74) *Attorney, Agent, or Firm*—C. A. Whealy

(57) ABSTRACT

A new and distinct cultivar of *Verbena* plant named 'Lan Pursar', characterized by its compact, low, outwardly spreading and decumbent plant habit; vigorous growth habit; freely branching habit; freely flowering habit; large purple and white "star"-patterned flowers; and resistance to Powdery Mildew.

1 Drawing Sheet

Botanical designation: *Verbena hybrida.*
Cultivar denomination: 'Lan Pursar'.

BACKGROUND OF THE INVENTION

The present invention relates to a new and distinct cultivar of *Verbena* plant, botanically known as *Verbena hybrida,* and hereinafter referred to by the name 'Lan Pursar'.

The new *Verbena* originated is a naturally-occurring branch mutation of a proprietary selection of *Verbena hybrida* identified as code number 1866-3, not patented. The new *Verbena* was discovered and selected by the Inventor on a single flowering plant within a population of plants of the proprietary selection grown in a controlled greenhouse environment in Gilroy, Calif. in February, 2005.

Asexual reproduction of the new *Verbena* by vegetative cuttings in a controlled greenhouse environment in Gilroy, Calif. since February, 2005, has shown that the unique features of this new *Verbena* are stable and reproduced true to type in successive generations.

SUMMARY OF THE INVENTION

The cultivar Lan Pursar has not been observed under all possible environmental conditions, The phenotype may vary somewhat with variations in environment such as temperature and light intensity, without, however, any variance in genotype.

The following traits have been repeatedly observed and are determined to be the unique characteristics of 'Lan Pursar'. These characteristics in combination distinguish 'Lan Pursar' as a new and distinct cultivar of *Verbena:*

1. Compact, low, outwardly spreading and decumbent plant habit.
2. Vigorous growth habit.
3. Freely branching habit.
4. Freely flowering habit.
5. Large purple and white "star"-patterned flowers.
6. Resistant to Powdery Mildew.

Plants of the new *Verbena* differ from plants of the parent selection in the following characteristics:

1. Plants of the new *Verbena* are more trailing than plants of the parent selection.
2. Plants of the new *Verbena* have larger leaves than plants of the parent selection.
3. Plants of the new *Verbena* and the parent selection differ in flower color pattern as plants of the parent selection have purple "mosaic"-patterned flowers.

Plants of the new *Verbena* can be compared to plants of the *Verbena* 'Lan Lav Star', disclosed in U.S. Plant Pat. No. 14,590. In side-by-side comparisons conducted in Gilroy, Calif., plants of the new *Verbena* differed from plants of 'Lan Lav Star' in the following characteristics:

1. Plants of the new *Verbena* were more trailing than plants of 'Lan Lav Star'.
2. Plants of the new *Verbena* had longer internodes than plants of 'Lan Lav Star'.
3. Plants of the new *Verbena* had brighter purple-colored flowers than plants of 'Lan Lav Star'.
4. Plants of the new *Verbena* had longer peduncles and shorter pedicels than plants of 'Lan Lav Star'.

BRIEF DESCRIPTION OF THE PHOTOGRAPH

The accompanying photograph illustrates the overall appearance of the new *Verbena.* This photograph shows the colors as true as it is reasonably possible to obtain in colored reproductions of this type. Colors in the photograph may differ slightly from the color values cited in the detailed botanical description which accurately describe the colors of the new *Verbena.* The photograph comprises a close-up view of a typical flowering plant of 'Lan Pursar'. Plants used in the photograph were grown in Gilroy, Calif. during the summer in an outdoor nursery and were about six months old when the photograph was taken.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Gilroy, Calif. during the spring in a greenhouse in 10-cm containers and under conditions and practices which approximate those generally used in commercial *Verbena* production. During the production of the plants, day temperatures ranged from 24° C. to 32° C. and night temperatures averaged 18° C. Measurements and numerical values represent averages for typical flowering plants. Plants were three months old when the description was taken and were pinched one time.

Botanical classification: *Verbena hybrida* 'Lan Pursar'.

Parentage: Naturally-occurring branch mutation of a proprietary selection of *Verbena hybrida* identified as code number 1866-3, not patented.

Propagation:

*Type.*—By vegetative cuttings.

*Time to initiate and develop roots.*—About two weeks.

*Root description.*—Fibrous, fleshy; white in color.

Plant description:

*Plant habit.*—Compact, low, outwardly spreading and decumbent plant habit. Freely branching habit with about four to eight primary lateral branches per plant each with multiple secondary branches; pinching enhances lateral branch development; dense and bushy plant habit. Vigorous growth habit.

*Plant height.*—About 10 cm to 13 cm.

*Plant diameter.*—About 40 cm to 50 cm.

Lateral branch description:

*Length.*—About 25 cm to 30 cm.

*Diameter.*—About 2.5 mm.

*Internode length.*—About 4 cm to 6 cm.

*Strength.*—Strong.

*Texture.*—Heavily hirsute with glandular hairs.

*Color.*—Close to 144B with irregular blotches of 166A.

Foliage description:

*Arrangement.*—Opposite, simple.

*Length.*—About 3.1 cm to 3.6 cm.

*Width.*—About 1.6 cm to 2.1 cm.

*Shape.*—Lanceolate.

*Apex.*—Obtuse to acute.

*Base.*—Truncate.

*Margin.*—Crenate.

*Texture, upper and lower surfaces.*—Hirsute with glandular hairs.

*Venation pattern.*—Pinnate.

*Color.*—Developing foliage, upper surface: Between 147A and 147B. Developing foliage, lower surface: Close to 137C. Fully expanded foliage, upper surface: Slightly darker than 147A; venation, close to 144B. Fully expanded foliage, lower surface: Close to 137C; venation, close to 144B.

*Petiole.*—Length: About 2 mm to 3 mm. Diameter: About 1.5 mm to 2 mm. Texture, upper and lower surfaces: Heavily hirsute with glandular hairs. Color, upper and lower surfaces: Close to 144B.

Flower description:

*Flower arrangement and habit.*—Salverform flowers arranged in hemispherical terminal umbels; flowers face upward or outward. Freely flowering habit with about 20 to 25 flowers per inflorescence.

*Natural flowering season.*—Plants flower continuously from the spring through the fall in California.

*Flower longevity.*—Flowers last about five to seven days on the plant. Flowers not persistent.

*Fragrance.*—None detected.

*Inflorescence diameter.*—About 4 cm to 5 cm.

*Inflorescence height.*—About 3.5 cm to 5 cm.

*Flowers.*—Appearance: Flared trumpet, corolla fused, five-parted. Diameter: About 1.8 cm to 2.2 cm. Tube length: About 1.7 cm to 1.8 cm.

*Flower buds.*—Length: About 7 mm to 10 mm. Diameter: About 3 mm. Shape: Tubular. Color: Close to N82A.

*Corolla.*—Arrangement: Single whorl of five fused petals. Petal lobe length: About 1 cm to 1.2 cm. Petal lobe width: About 1 cm to 1.1 cm. Petal lobe shape: Roughly obcordate. Petal lobe apex: Emarginate. Petal margin: Entire. Petal texture, upper and lower surfaces: Papillose. Color: Petal lobe, when opening, upper surface: Center, slightly darker than N81A; towards the margins, "star" pattern, close to 155D with random irregular spots, close to N81A. Petal lobe, when opening, lower surface: Center, close to N82C; towards the margins, "star" pattern, close to 155D with random irregular spots, close to N82A. Petal lobe, fully opened, upper surface: Center, close to N82A; towards the margins, "star" pattern, close to 155D with random irregular spots, close to N82A. Petal lobe, fully opened, lower surface: Center, close to N82C; towards the margins, "star" pattern, close to 155D with random irregular spots, close to N82A. Throat: Close to 155C. Tube: Close to 155C.

*Calyx.*—Arrangement: One single narrow calyx tube per flower with five fused sepals. Sepal length: About 1.1 cm to 1.3 cm. Sepal width: About 1 mm to 1.5 mm. Sepal shape: Lanceolate. Sepal apex: Acute. Sepal base: Fused. Sepal margin: Entire. Sepal texture, upper and lower surfaces: Hirsute with glandular hairs. Sepal color, upper and lower surfaces: Close to 138A.

*Peduncles.*—Length: About 4.5 cm to 6.5 cm. Diameter: About 1.5 cm to 2 mm. Strength: Strong. Texture: Hirsute with glandular hairs. Color: Close to 138B.

*Pedicels.*—Flowers are sessile.

*Reproductive organs.*—Stamens: Quantity/arrangement: Four per flower, adnate to corolla tube. Filament color: Close to N155C. Anther shape: Elliptic. Anther length: Less than 1 mm. Anther color: Close to 4C. Pollen amount: Moderate. Pollen color: Close to 4C. Pistils: Minute. Quantity: One per flower. Pistil length: About 2 cm to 2.1 cm. Stigma shape: Roughly lanceolate. Stigma color: Close to 144A. Style color: Towards the apex, close to 145B; towards the base, close to 155D.

*Fruits/seed.*—Fruit and seed development have not been observed.

Garden performance: Plants of the new *Verbena* have been observed to tolerate wind, rain and a wide range of temperatures.

Pathogen/pest resistance: Plants of the new *Verbena* have been observed to be resistant to Powdery Mildew. Plants of the new *Verbena* have not been observed to be resistant to pests and other pathogens common to *Verbenas*.

It is claimed:

1. A new and distinct *Verbena* plant named 'Lan Pursar' as illustrated and described.

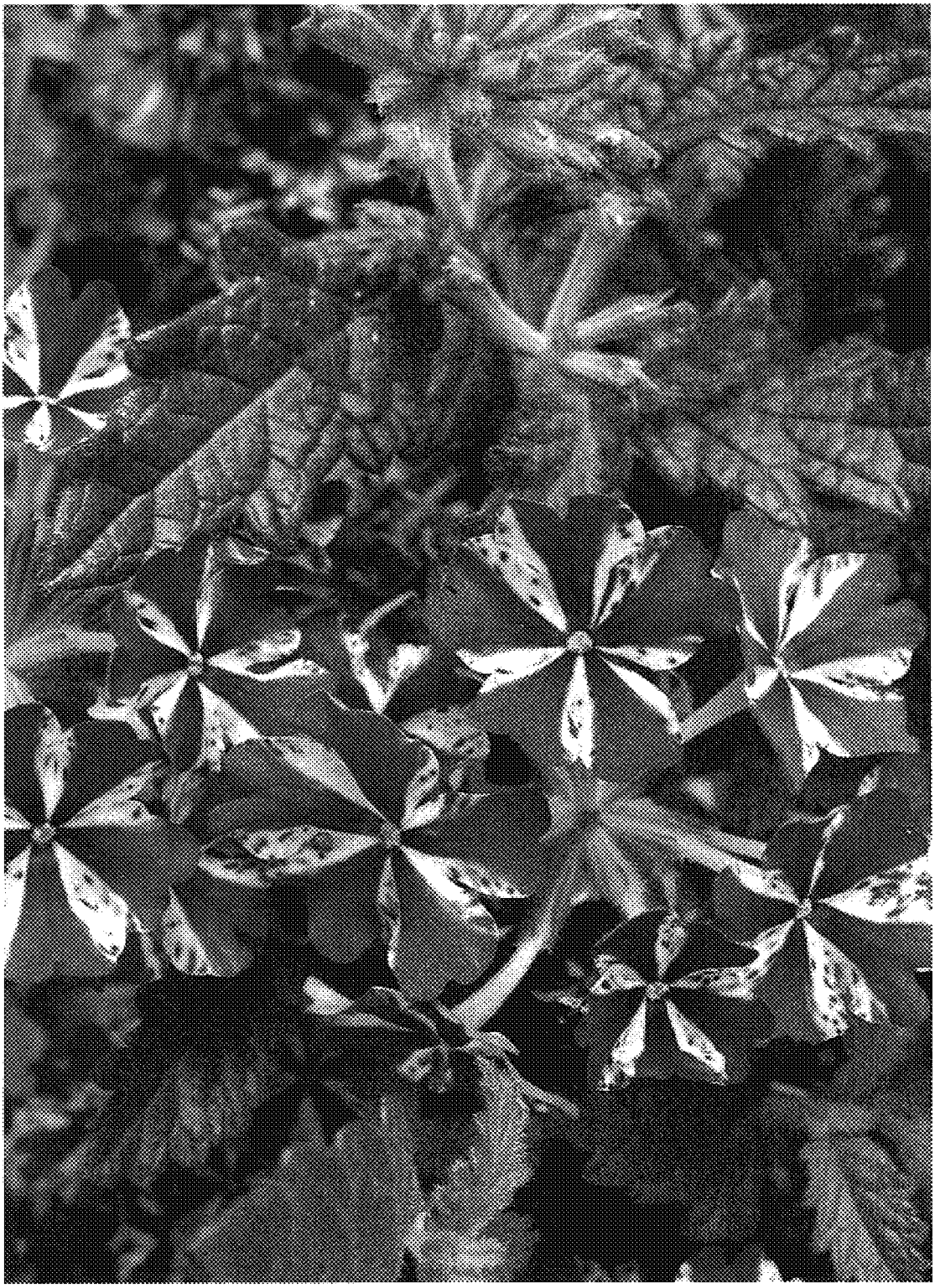

* * * * *